United States Patent [19]

Matsutani

[11] 4,306,443

[45] Dec. 22, 1981

[54] CRIMPING APPARATUS

[75] Inventor: Kanji Matsutani, Takanezawa, Japan

[73] Assignee: Kabushiki Kaisha Matsutani Seisakusho, Tochigi, Japan

[21] Appl. No.: 85,095

[22] Filed: Oct. 15, 1979

[30] Foreign Application Priority Data

Jan. 29, 1979 [JP] Japan .................................. 54-09407

[51] Int. Cl.³ .............................. B21J 7/10; B21J 9/18
[52] U.S. Cl. ....................................... 72/434; 72/416; 72/452
[58] Field of Search ................. 72/452, 431, 433, 434, 72/416, 412

[56] References Cited

U.S. PATENT DOCUMENTS

| | | | |
|---|---|---|---|
| 3,611,551 | 10/1971 | Shave | 128/339 |
| 3,980,177 | 9/1976 | McGregor | 128/339 |
| 4,072,041 | 2/1978 | Hoffman | 72/416 |

FOREIGN PATENT DOCUMENTS

| | | | |
|---|---|---|---|
| 530780 | 10/1921 | France | 72/434 |
| 30963 | 8/1920 | Norway | 72/434 |
| 83133 | 4/1935 | Sweden | 72/434 |
| 59705 | 3/1912 | Switzerland | 72/434 |
| 98359 | 3/1923 | Switzerland | 72/434 |
| 197641 | 1/1924 | United Kingdom | 72/433 |

*Primary Examiner*—Gene P. Crosby
*Attorney, Agent, or Firm*—James C. Wray

[57] ABSTRACT

A hollow end of a needle has an end of a suture crimped therein by crimping dies. A cam drives a table downward. The table pulls a spring which in turn pulls a guide and an adjusting screw which urges a block toward the table. One end of an arm is connected to the block, another end of the arm is connected to a pivot. A link at an intermediate position on the arm is connected to drive a ram against a movable die, driving the die to crimp the needle end. The ram carries a pressure means which urges the movable die toward the fixed die when the ram is not contacting the movable die so that the needle is held between the dies with a less-than-crimping force. The cam moves the table downward to apply the holding force and then moves the table further downward to apply the crimping force. When the adjusted crimping force is met, the spring stretches and allows the block to move away from the table to prevent excessive crimping force. The cam then moves the table to move the ram away from the movable die and continues the holding force so that the needle can be turned. The cam again applies crimping force and then holding force to allow the suture to be pulled and the crimp tested. Then the cam permits the pressure means to move away from the ram so that the movable die may be lifted by a leaf spring.

14 Claims, 5 Drawing Figures

CRIMPING APPARATUS

TECHNICAL FIELD

This invention relates to a crimping apparatus for attaching a surgical needle to a suture.

In a small crimping apparatus having a pair of dies which are adapted to crimp a surgical needle on a suture, it is usual to arrange the dies so that when they close, a predetermined space is left between them, i.e., a so-called predetermined space crimping. However, the materials to be crimped, such as a needle and suture, usually vary more or less in their sizes, particularly in the outer diameter of the needle or suture, or the inner diameter of the needle end hollow into which the suture is inserted. When subjected to the predetermined space crimping, such materials receive crimping forces of differing strengths depending upon their sizes and thus, the suture tends to be clipped off when too much crimping force is exerted, or the suture tends to be slipped out from the needle when the crimping force is not adequate.

SUMMARY OF THE INVENTION

It is accordingly an object of the present invention to eliminate the above-mentioned disadvantages by providing an apparatus capable of crimping the materials under a predetermined crimping load regardless of variation of their sizes.

Thus, the present invention provides a crimping apparatus which comprises a pair of dies operable to crimp therebetween a needle end over a suture, a reciprocating table movable to produce a crimping force, and a load adjusting spring means to transmit the crimping force of the reciprocating table to said dies, wherein the arrangement is such that when a responsive force created by the crimping of the dies is smaller than the crimping force, said dies and reciprocating table move in unison, but when the responsive force becomes equal to or greater than the crimping force, said dies and reciprocating table no more move in unison.

According to another aspect of the invention, the apparatus is further provided with a spring to urge the dies to open and a pressure spring to urge the dies to close, so that the dies resiliently hold a needle in between, thus providing a preliminary needle-holding mode in which a needle can be checked and corrected for its positioning between the dies, in which the needle can be turned at an angle of 90° after a first crimping and for the subsequent second crimping, and in which a suture after crimping can be tested for its resistance against pulling.

DETAILED DESCRIPTION OF THE DRAWINGS

Figure 1:
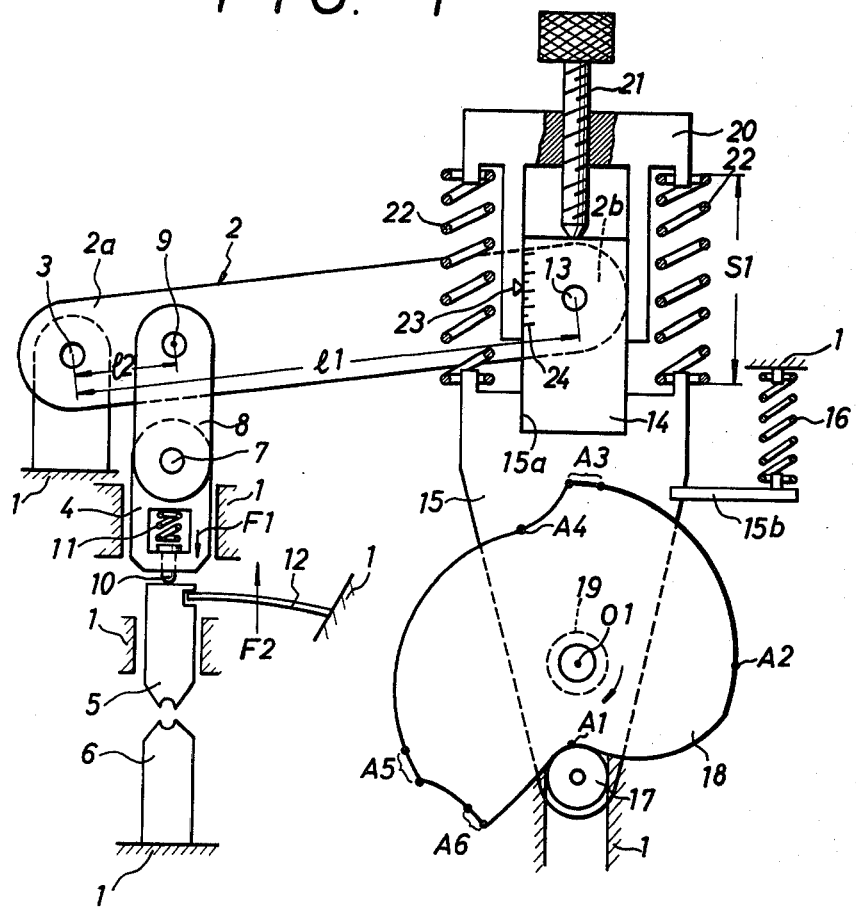
FIG. 1 is a schematic front view of an embodiment of the present invention in which the dies are open.

Referring to FIG. 1, reference numeral 1 designates a body of the crimping apparatus, as shown fragmentally and schematically. A rocker arm 2 is swingably connected at its base end 2a to a horizontal pin 3 which is mounted on a stand on the body 1. Beneath the rocker arm 2, a ram 4 is provided, and beneath the ram 4, an upper die 5 is located which is movable up and down. Beneath the upper die 5, a lower die 6 is secured to the body 1.

A connecting arm 8 is rotatably mounted at its lower end on a pin 7 of the ram 4 and at its upper end on a pin 9 which is provided near the base end 2a of the rocker arm 2.

The ram 4 has on its lower side a pressure pin 10 protrusile or retractile from the pressure of ram 4 surface facing the upper die 5. A pressure spring 11 is provided to normally urge the pressure pin 10 to protrude downward.

The upper die 5 is normally urged upward by a wire spring 12 which is secured to the body 1. The spring force $F_2$ of the wire spring 12 is smaller than the spring force $F_1$ of the pressure spring 11, and accordingly the upper die 5 is normally spaced from the ram 4 and is in contact with the pressure pin 10.

A block member 14 is rotatably attached by a pin 13 at the front end 2b of the rocker arm 2. Beneath the block member, there is provided a reciprocating table 15 functioning as a cam follower, movable up and down. The lower end of the block member 14 is slidably received in a recess 15a formed on the upper surface of the reciprocating table 15. The table 15 is urged upward by a spring 16 which is provided between the body 1 and an arm 15b extending from the side of the table. Thus, a roller 17 mounted on the table 15 is always in contact with the lower periphery of the cam 18 and is guided in its up and down movements by the body 1. A shaft 19 of the cam 18 extends at right angle relative to the plane of the sheet of FIG. 1 and is rotatably supported by bearings (not shown) provided on the body 1. The shaft 19 is adapted to be driven by a motor (not shown) via a belt. The up and down movements of the reciprocating table 15 are thus controlled by the rotation of the cam 18.

A guide 20 slidably encloses the upper portion of the block member 14 and is movable up and down. The guide has a load adjusting screw 21 for adjusting the relative positioning of the guide 20 to the block member 14, i.e., the distance between the guide 20 and the reciprocating table 15.

One or more load adjusting tension springs 22 are provided between the guide 20 and the reciprocating table 15 so that the block member 14 is urged downward and normally rests on the reciprocating table 15. A spring force $F_3$ corresponding to the length $S_1$ of spring 22 is converted into a value of a crimping force F, which will be explained later, and is indicated as such by an indicator pointer 23 against a load indicator scale 24 provided on the block member 14. Alternatively, the indicator pointer 23 may be provided on the block member 14, while providing the load indicator scale on the guide 20. The spring force $F_3$ of the spring 22 is considerably larger than the spring forces $F_1$ and $F_2$ of the above-mentioned springs 11 and 12.

Now, the operation of the apparatus will be described.

Figure 3:
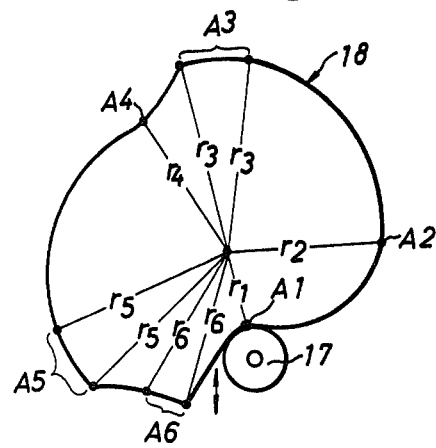
FIG. 3 is a front view illustrating the shape of the cam.
Figure 4:
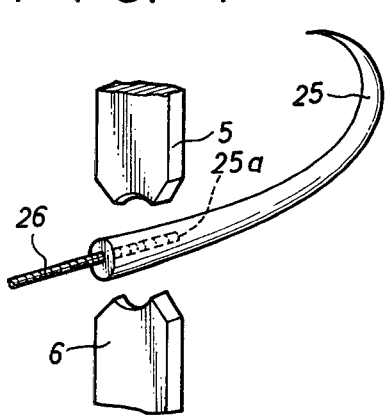
FIG. 4 is an enlarged perspective view illustrating the manner of crimping a needle with a pair of dies.

When the pair of dies 5 and 6 are open as shown in FIG. 1, the cam 18 takes a position as shown in FIG. 3 where it is in contact with the roller 17 at point $A_1$. A distance $r_1$ between point $A_1$ and the center $O_1$ of rotation of the cam 18 is the smallest. Accordingly, the reciprocating table 15 is at the uppermost position with the block member 14 sitting thereon. A surgical needle 25 with a suture 26 inserted in its rear end hollow 25a is placed between the open dies 5 and 6, for instance as shown in FIG. 4.

When the cam 18 rotates in a direction as shown by an arrow in FIG. 1, the reciprocating table 15, spring 22, guide 20 and block member 14 move together downward, and the rocker arm 22 rotates clockwise as shown in FIG. 1 and the upper die 5 moves downward. When the cam 18 rotates to a position where point $A_2$ comes into contact with the roller 17, the distance $r_2$ becomes greater than the distance $r_1$ and the upper die resiliently presses the needle 25 by the spring action of the pressure spring 11 against the lower die 6, i.e., in a preliminary holding mode wherein the ram 4 itself is not yet in contact with the upper die 5. In this preliminary holding mode, checking is made to see that the needle is properly placed between the dies 5 and 6 and if necessary, the position of the needle is corrected.

Figure 2:
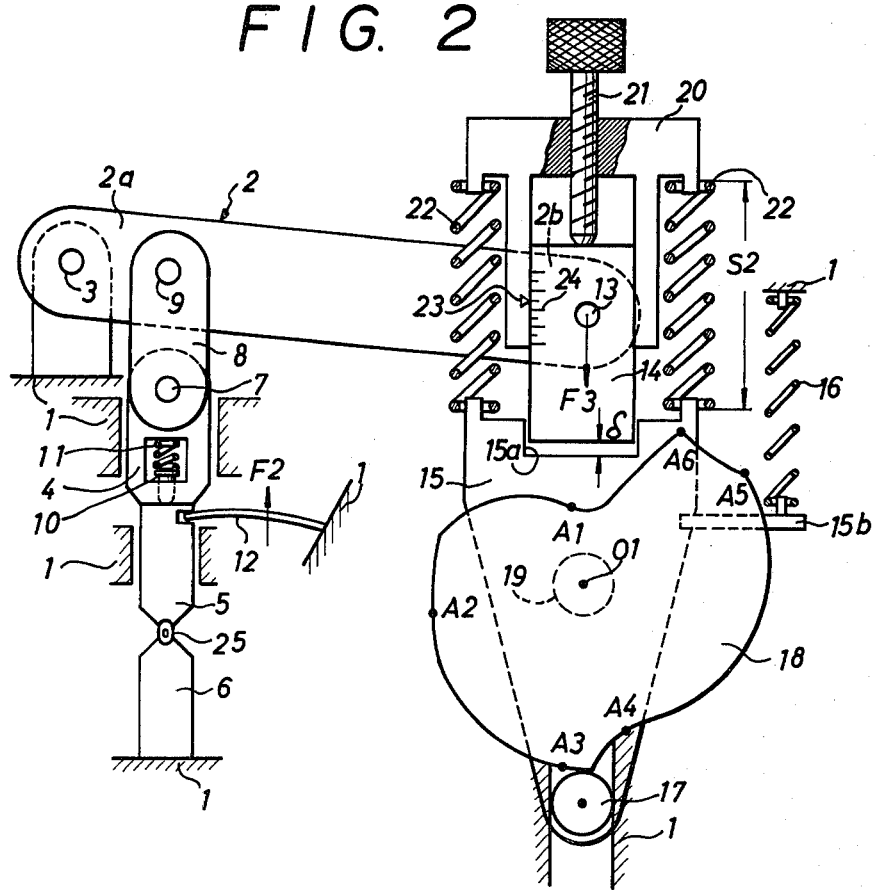
FIG. 2 is a schematic view similar to FIG. 1 but illustrates the dies in the crimping position, i.e., the closed position.

Upon further rotation of the cam 18, an intermediate point between points $A_2$ and $A_3$ comes into contact with the roller 17, and then the ram 4 is in direct contact with the upper die 5, whereafter the ram 4 and upper die 5 move together downward to crimp the needle under a predetermined load. The crimping force F is represented by the formula $$F = \frac{l_1}{l_2} F_3 - F_2,$$

wherein $l_1$ is a distance between the pins 3 and 13, $l_2$ is a distance between the pins 3 and 9, $F_3$ is a spring force of the springs 22 of a predetermined length $S_1$, exerted on the pins 13, and $F_2$ is a spring force of the spring 12. A responsive force against the ram 4, i.e., the force directed upward in FIG. 2 increases while it is still smaller than the crimping force F. Upon further rotation of the cam 13, the reciprocating table 15 moves downward with the springs 22 maintaining its predetermined length $S_1$, and the guide 20 and the block member 14 to which the rocker arm is connected, also move together downward, thereby crimping the needle 25 until the responsive force against the ram 4 becomes equal to the crimping force F.

After the responsive force against the ram 4 becomes greater than the crimping force, the arm 2, or the block member 14 no longer moves downward and will not follow the downward movement of the reciprocating table 15, and the springs 22 expand beyond the predetermined length $S_1$. When the cam 13 comes to a position where point $A_3$ is in contact with the roller 17, the table 15 is located at the lowest position and the springs 22 are most expanded. The spring force $F_3$ of the spring 33 increases in correspondence with the expansion, and the crimping is done with the predetermined load based on this increased spring force. The maximum amount of the expansion of the spring 22 is represented by the space $\delta$ between the block member 14 and the reciprocating table 15, namely the length $S_2$ of the spring in the most expanded state minus the predetermined length $S_1$.

If the needles 25 differ from each other in their diameters, the differences are amplified by the lever effect of the rocker arm 2, and the space $\delta$ fluctuates accordingly. However, where a spring constant of the spring 22 is set to be small, such differences in their diameters are negligible and do not affect the spring force $F_3$ of the spring 22.

After the first crimping operation, the cam 18 further rotates to come to positions where points $A_4$, $A_5$ and $A_6$ come into contact with the roller 17, respectively. The distances $r_4$, $r_5$ and $r_6$ of these points from the center of rotation equal to $r_2$, $r_3$ and $r_2$, respectively. In the preliminary holding mode at the position $A_4$, the needle 25 is turned at an angle of 90° and then the second crimping operation is carried out in a manner similar to the one described above. After the completion of the second crimping operation, the cam comes to the initial position where the point $A_1$ is in contact with the roller 17. The relation of the distances from each point to the center of rotation is $r_1 < r_2 = r_4 = r_6 < r_3 = r_5$. At the point $A_6$, a pulling test of the suture after the crimping operation is carried out.

The cam 18 may steadily and continuously be rotated, or the rotation thereof may be stopped at each of points $A_1$ to $A_6$ or at points $A_1$, $A_2$, $A_4$ and $A_6$ by operation of a foot switch by an operator. The stopping of the rotation may be carried out automatically.

According to the present invention, the crimping operation can be carried out under a predetermined load. Under the following conditions, the crimping operation was carried out, and among one thousand needles crimping over the sutures, none showed "slipping off" or "clipping off" of the sutures.

Crimping Conditions (1) Needle 25

Material: stainless steel (SUS 304, AISI 304)
Hardness: HV 205 at the portion to be crimped (HV 550 at the main body portion)
Outer diameter: 0.5 mm. (±0.01 mm.)
Inner diameter (hollow 27a): 0.26 mm. (±0.01 mm.)
Length of the portion to be crimped: 0.8 mm.

(2) Suture 26

Material: Nylon (monofilament)
Outer diameter: 0.23 mm. (±0.02 mm.)

(3) Crimping force: 30 kg (between the dies 5 and 6)

The crimping force is adjustable depending on the diameter of the needles to be crimped. The adjustment can be done quite easily and accurately by rotating the screw 21. It is advantageous that the crimping force be determined beforehand by testing a few sample needles.

Thus, having described the invention, it is apparent that the present invention provides a simple and compact apparatus whereby the crimping operation can be done under an accurate predetermined load. The apparatus of the present invention is effectively used for crimping small objects such as eyeless needles.

Figure 5:
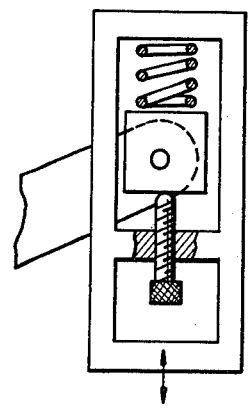
FIG. 5 shows another embodiment illustrating a predetermined load adjusting portion in which a pressure spring is employed.

The present invention is not restricted to the above described embodiment. For instance, the reciprocating table 15 may be driven by a cylinder and piston or by manual operation (by a foot) instead of the motor and cam. Further, the load-adjusting spring 22 may be a pressure spring as shown in FIG. 5 instead of the expansion spring. Still further, the rocker arm 2 may be omitted and the spring action may be transmitted direct to the connecting arm 8 or the ram 4.

I claim:

1. A crimping apparatus for attaching a surgical needle to
    a suture, which comprises:
    a pair of dies operable to crimp therebetween a needle end over a suture received in a hollow in the needle end,
    a reciprocating table means movable to produce a crimping force, and
    a load-adjusting spring means to transmit the crimping force of the reciprocating table means to said dies through a pivot arm, said arm having a fulcrum at one end,
    the arrangement being such that when a responsive force created by the crimping of the dies is smaller than the crimping force, said dies and reciprocating table means move in unison but when the responsive force becomes equal to or greater than the crimping force, said dies and reciprocating table means no more move in unison.

2. A crimping apparatus for attaching a surgical needle to a suture, which comprises:
    a pair of dies operable to crimp therebetween a needle end over a suture received in a hollow in the needle end,
    a reciprocating table means movable to produce a crimping force, and
    a load-adjusting spring means to transmit the crimping force of the reciprocating table means to said dies,
    the arrangement being such that when a responsive force created by the crimping of the dies is smaller than the crimping force, said dies and reciprocating table means move in unison but when the responsive force becomes equal to or greater than the crimping force, said dies and reciprocating table means no more move in unison,
    and further comprising a spring to urge the dies to open and a pressure spring to urge the dies to close, thereby providing a preliminary needle holding mode in which a needle can be checked and corrected for its positioning between the dies, in which the needle can be turned at an angle of 90°, and in which a suture after crimping can be tested for its resistance against pulling.

3. A crimping apparatus for attaching a surgical needle to a suture, which comprises:
    a pair of dies operable to crimp therebetween a needle end over a suture received in a hollow in the needle end,
    a reciprocating table means movable to produce a crimping force, and
    a load-adjusting spring means to transmit the crimping force of the reciprocating table means to said dies,
    the arrangement being such that when a responsive force created by the crimping of the dies is smaller than the crimping force, said dies and reciprocating table means move in unison but when the responsive force becomes equal to or greater than the crimping force, said dies and reciprocating table means no more move in unison,
    wherein the pair of dies comprises a first fixed die and a second movable die, each of the dies having a complementary recess for receiving a needle end, and further comprising a ram means for contacting the movable die and driving the movable die toward the fixed die, pressure means extending from the ram means toward the movable die for contacting the movable die and for urging the movable die toward the fixed die in absence of contact of the ram means with the movable die.

4. A crimping apparatus for attaching a surgical needle to a suture, which comprises:
    a pair of dies operable to crimp therebetween a needle end over a suture received in a hollow in the needle end,
    a reciprocating table means movable to produce a crimping force, and
    a load-adjusting spring means to transmit the crimping force of the reciprocating table means to said dies,
    the arrangement being such that when a responsive force created by the crimping of the dies is smaller than the crimping force, said dies and reciprocating table means move in unison but when the responsive force becomes equal to or greater than the crimping force, said dies and reciprocating table means no more move in unison,
    and further comprising a cam means connected to drive the reciprocating table means and wherein the load-adjusting spring means comprises a guide spaced from the table, one or more springs connected between the table and the guide, a block normally resting on the table and an adjusting screw connected between the guide and the block for urging the block toward the table and urging the guide away from the table and further comprising means for connecting the block to one of the dies.

5. The crimping apparatus as claimed in claim 4 wherein the connecting means comprises an arm having one end connected to a pivot and having another end connected to the block and having an intermediate portion connected via link means to a movable die in the pair of dies.

6. The crimping apparatus as claimed in claim 5 wherein the link means comprises a ram means for contacting the movable die and driving the movable die toward a fixed die, pressure means extending from the ram means toward the movable die for contacting the movable die and for urging the movable die toward the fixed die in absence of contact of the ram means with the movable die.

7. The crimping apparatus as claimed in claim 6 further comprising spring means connected to the movable die for urging the movable die toward the ram means, wherein the spring means connected to the movable die produces less force than the pressure means.

8. A method of crimping an end of the surgical needle about a suture comprising inserting a surgical needle and having a suture positioned therein in a pair of dies, moving the dies together and holding the needle between the dies with a holding force, moving the dies toward each other with a crimping force, selectively adjusting the crimping force, maintaining the crimping force, releasing the crimping force without releasing the holding force, turning the needle and suture, applying a crimping force, holding the crimping force, releasing the crimping force and maintaining the holding force and subsequently releasing the holding force.

9. A crimping apparatus comprising
    a pair of dies, reciprocating table means movable to produce a crimping force, and load adjusting spring means to transmit the crimping force of the reciprocating table means to said dies, the arrangement being such that when a responsive force created by the crimping of the dies is smaller than the crimping force, said dies and reciprocating table means move in unison, but when the responsive force becomes equal to or greater than the crimping force, said dies and reciprocating table means no more move in unison, wherein the pair of dies comprises a first fixed die and a second movable die, ram means for contacting the movable die and driving the movable die toward the fixed die, and pressure means extending from the ram means toward the movable die for contacting the movable die and for urging the movable die toward the fixed die in absence of contact of the ram means with the movable die.

10. Crimping apparatus comprising a pair of dies, reciprocating table means movable to produce a crimping force, load adjusting spring means to transmit the crimping force of the reciprocating table means to said dies, the arrangement being such that when a responsive force created by the crimping of the dies is smaller than the crimping force, said dies and reciprocating table means move in unison, but when the responsive force becomes equal to or greater than the crimping force, said dies and reciprocating table means no more move in unison, wherein the load-adjusting spring means comprises a guide spaced from the table, one or more springs connected between the table and the guide, a block normally resting on the table, and means for connecting the block to one of the dies.

11. The apparatus of claim 10 further comprising cam means connected to drive the reciprocating table means.

12. The crimping apparatus as claimed in claim 10 wherein the connecting means comprises an arm having one end connected to a pivot and having another end connected to the block and having an intermediate portion connected via link means to a movable die in the pair of dies.

13. The crimping apparatus as claimed in claim 12 wherein the link means comprises a ram means for contacting the movable die and driving the movable die toward a fixed die, pressure means extending from the ram means toward the movable die for contacting the movable die and for urging the movable die toward the fixed die in absence of contact of the ram means with the movable die.

14. The crimping apparatus as claimed in claim 13 further comprising spring means connected to the movable die for urging the movable die toward the ram means, wherein the spring means connected to the movable die produces less force than the pressure means.

* * * * *